United States Patent
Motulla

(10) Patent No.: US 6,335,626 B1
(45) Date of Patent: Jan. 1, 2002

(54) METHOD AND DEVICE FOR DETERMINING A PARAMETER FOR A METALLIZATION BATH

(75) Inventor: Gerald Motulla, Berlin (DE)

(73) Assignee: Pac Tech - Packaging Technologies GmbH (DE)

( * ) Notice: Subject to any disclaimer, the term of this patent is extended or adjusted under 35 U.S.C. 154(b) by 0 days.

(21) Appl. No.: 09/486,250
(22) PCT Filed: Aug. 11, 1998
(86) PCT No.: PCT/DE98/02301
§ 371 Date: Feb. 22, 2000
§ 102(e) Date: Feb. 22, 2000
(87) PCT Pub. No.: WO99/10734
PCT Pub. Date: Mar. 4, 1999

(30) Foreign Application Priority Data

Aug. 21, 1997 (DE) .......................... 197 36 113

(51) Int. Cl.⁷ ..................... G01R 27/00; B05D 5/12
(52) U.S. Cl. ........................ 324/691; 427/8; 427/98
(58) Field of Search ............................ 324/514, 527, 324/699, 693, 691, 765; 427/8, 98

(56) References Cited

U.S. PATENT DOCUMENTS

| | | | | |
|---|---|---|---|---|
| 4,034,126 A | * | 7/1977 | Funnakosshi et al. ......... 427/8 |
| 4,165,270 A | * | 8/1979 | Ost et al. .................... 204/401 |
| 4,569,744 A | * | 2/1986 | Walker ....................... 204/284 |
| 4,824,693 A | * | 4/1989 | Schlipf et al. ................ 427/98 |
| 4,882,537 A | | 11/1989 | Silverman |
| 5,219,765 A | * | 6/1993 | Yoshida et al. ............... 438/10 |
| 5,491,097 A | * | 2/1996 | Ribi et al. ................... 436/518 |
| 5,795,619 A | * | 8/1998 | Lin et al. .................... 427/123 |

FOREIGN PATENT DOCUMENTS

DE 292 938 A5 8/1991

OTHER PUBLICATIONS

Akihiro Endo, Dec. 24, 1987, Patents Abstracts of Japan C-502 Jun. 8, 1988 vol. 12/No. 198.

* cited by examiner

Primary Examiner—Safet Metjahic
Assistant Examiner—Vincent Q. Nguyen
(74) Attorney, Agent, or Firm—McGlew and Tuttle, P.C.

(57) ABSTRACT

A method and device are provided for determining a parameter for the reproducible production of raised contact metallizations (24, 25) on terminal areas of a substrate. Metallization material is deposited in a metallization bath. A test substrate is employed having at least two terminal areas adjacent at a defined spacing. The substrate is introduced into the metallization bath (10) and the parameter is determined from the variation in an electrical quantity as a consequence of an electrical contact resulting to from the deposition of the metallization material for building up the contact metallizations (24, 25) on the adjacent terminal areas.

16 Claims, 3 Drawing Sheets

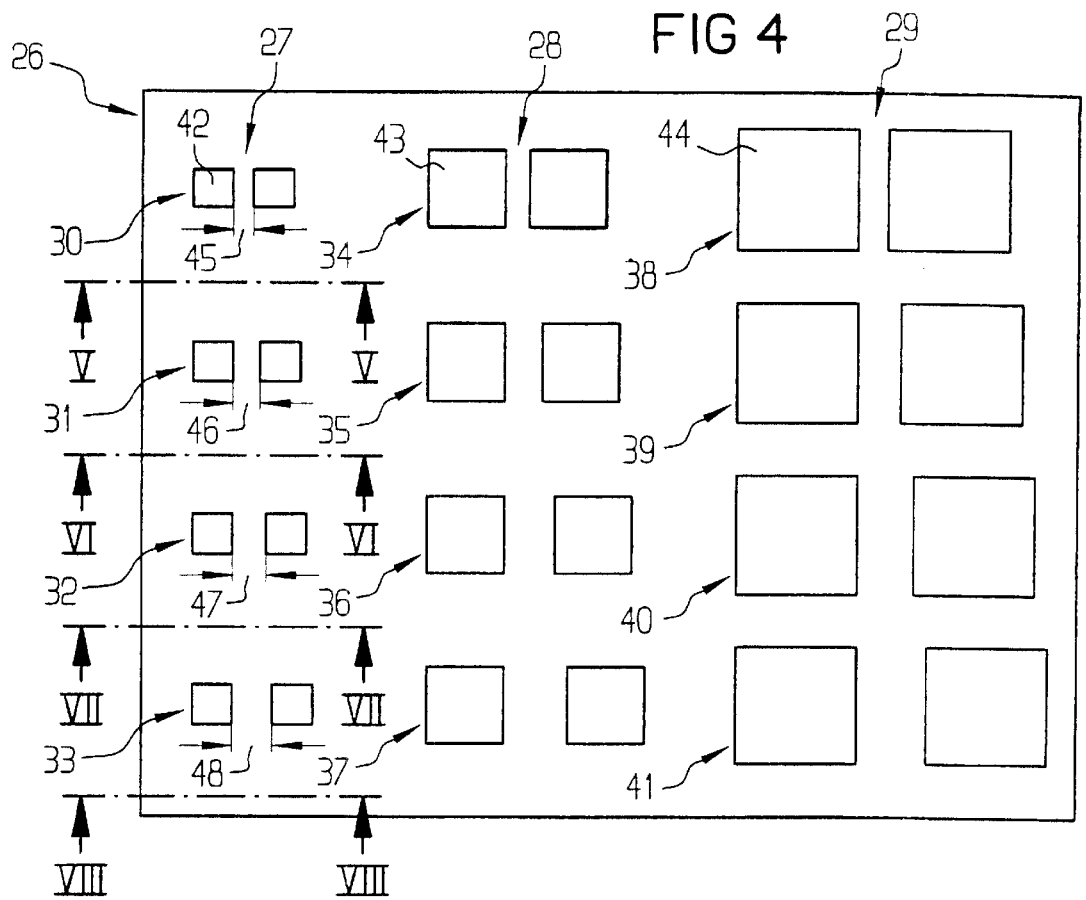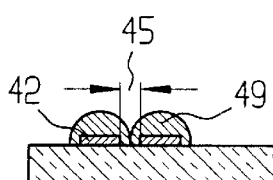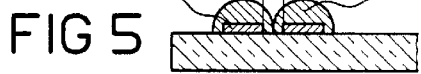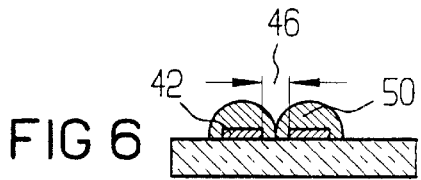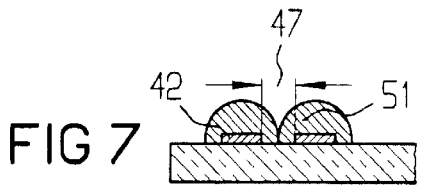

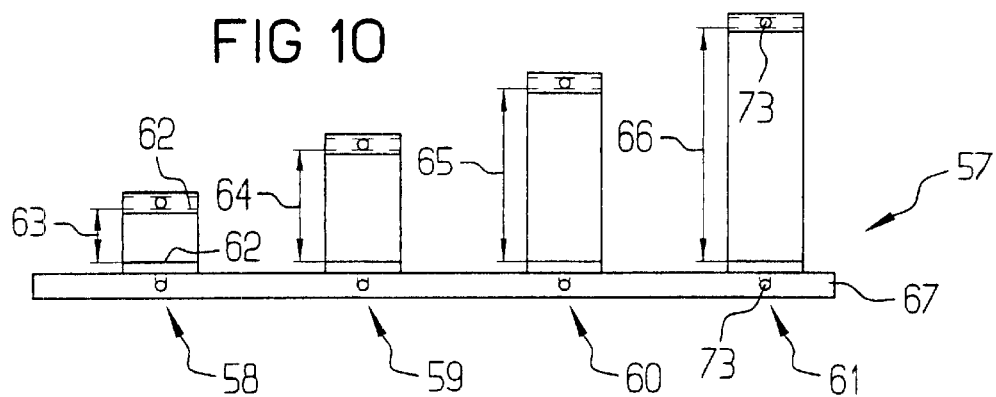
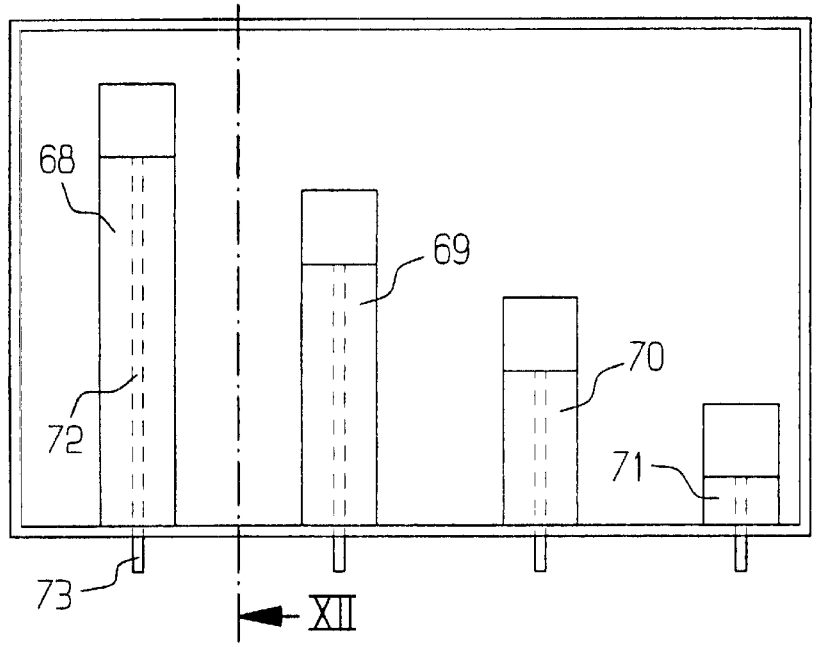
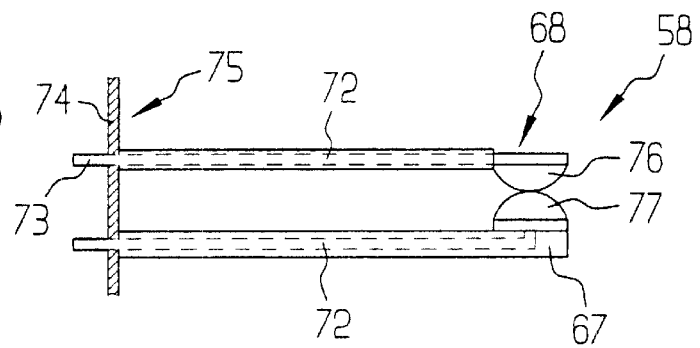

METHOD AND DEVICE FOR DETERMINING A PARAMETER FOR A METALLIZATION BATH

FIELD OF THE INVENTION

The present invention relates to a method for determining a parameter for the reproducible, production of raised contact metallizations on terminal areas of a substrate by means of depositing a metallization material in a metallization bath.

BACKGROUND OF THE INVENTION

In the production of raised contact metallizations, which are also described in technical terminology as "bumps", on terminal areas of a substrate, such as, for example, a chip or a carrier substrate that serves to mount chips or other electronic components, measures have been proved necessary in practice that make possible reproducibility of the production method in order to be able to produce bumps with uniform morphology. This applies regardless of the method chosen for the bump production, in particular for methods in which the bumps are produced by a metal deposition in a metallization bath. This can be done electrolytically or by wet-chemistry.

SUMMARY AND OBJECTS OF THE INVENTION

The object of the present invention is to propose a method for determining a parameter that makes possible a simple monitoring of the processes in a metallization bath in order to be able to produce reproducible bumps in regard to their morphology.

In accordance with a first solution of the invention, a method is proposed in which, according to the invention, a test substrate having at least two terminal areas adjacent at a defined spacing is introduced into the metallization bath and the parameter is determined from the variation in an electrical quantity as a consequence of an electrical contact resulting from the buildup of contact metallizations on the adjacent terminal areas.

In the method according to the invention, the body contact between the contact metallizations that results from the continuous buildup of the contact metallizations on the terminal areas induces an electrical signal that, given a defined, that is to say known spacing between the terminal areas, makes it possible to draw a conclusion about at least the area extent of the contact metallization In an isotropic deposition process of the metallization material dissolved in the metallization bath on the terminal areas of the substrate, that is to say given a uniform "growth" of the metallization material on the surface and also in the peripheral or edge regions of the terminal area, direct conclusions are in addition possible about the shape of the raised contact metallizations.

It has proved particularly advantageous if the abovementioned parameter is determined from the variation in the electrical resistance of an electrical measuring circuit encompassing the terminal areas.

According to another aspect of the invention, a test substrate having at least one terminal area is introduced into the metallization bath and the parameter is determined from the measurement of an electrical quantity due to the mass of the contact metallization on the terminal area. In contrast to the abovementioned fist achievement, in this case, conclusions about the morphology of the individual contact metallization are not drawn from the relationship between two contact metallizations deposited on terminal areas adjacent at a defined spacing, but, on the contrary, from the metallization mass formed on the terminal area during the deposition process, which metallization mass varies the electrical properties of the unit formed from the terminal area and the metallization mass.

In this connection, it is particularly advantageous if the parameter is to determined from the value of the electrical resistance of an electrical measuring circuit connected to the terminal area. This variant of the method according to the invention is based on the fact that, in addition to the density of the metallization material, the contact metallization cross section forming on the terminal area and also the length of the contact metallization formed on the terminal area determine the value of the ohmic resistance. In the case of known electrical quantities of the terminal area, direct conclusions can be drawn therefrom about the morphology of the contact metallization, in particular in the case of an isotropic deposition process.

In order to make possible a determination of the parameter that is substantially unaffected by the measurement current, it is proposed, proceeding from the principle of the achievement on which the two achievements according to the invention are based, namely the determination of a parameter based on electrical quantities determined in an electrical measuring circuit, to close the electrical measuring circuit for determining the electrical quantity, that is to say, for example, the resistance, only intermittently, preferably periodically. As a result it is possible, for example, to substantially suppress galvanic effects as a consequence of current flow between the terminal areas or between the metallization bath and the terminal area or terminal areas on a purely wet chemical deposition process.

In practice, the influence of so-called "stabilizing components" on the deposition process or the morphology of the contact metallizations deposited in a metallization bath provided with such stabilizing components has proved appreciable in some cases. In particular, it has been found that even small deviations in the metering of such stabilizing components in a metallization bath have disproportionately large effects on the morphology of the contact metallizations deposited. This is due substantially to the fact that the stabilizing components, which are intended to prevent the decomposition of the metallization baths or an undesired deposition of the metallization material on the walls of the bath containers, have a diffusion behaviour that acts against the desired deposition on the terminal areas. In addition, the behaviour of many stabilizing components, such as, for example, lead, proves to be nonlinear with regard to the diffusion into the sure of the terminal areas, which are normally designed as aluminum pads, so that in the peripheral regions of the terminal areas a greater deposition-inhibiting effect can be detected than in the region of the surface of the terminal areas. The use of stabilizing components in a metallization bath therefore results in appreciable effects on the morphology of the contact metallizations deposited on the terminal areas. Thus, it has proved necessary to monitor the concentration of the stabilizing components in the metallization bath continuously in order to be able to produce contact me metallizations that are constant with regard to their morphology.

On the basis of the relationships cited above, it proves particularly advantageous it in the case of the method according to the invention, the concentration of a bath stabilizer added to the metallization bath is determined as parameter. In a preferred variant of the method with regard to this application case, the test substrate is provided with a plurality of terminal area arrangements that each comprise two terminal areas assigned to one another with a defined contact spacing, the contact spacings varying in the individual terminal area arrangements and the test substrate is immersed for a predetermined time interval in the metallization bath. During said time interval, the electrical resistance between the terminal areas of the respective terminal area arrangements is repeatedly measured and the stabilizer concentration is determined as a function of the maximum contact spacing of the terminal areas with short-circuit contact as a result of comparison with contact spacing reference values for known stabilizer concentrations.

Furthermore, it also proves very advantageous if the method according to the invention is used as parameter for determining the deposition rate of the metallization material in the metallization bath during the formation of the contact metallization.

In accordance with a preferred variant of the method, to determine the deposition rate, the test substrate, which is provided with at least one terminal area arrangement that comprises in each case two terminal areas assigned to one another with a defined contact spacing, is immersed in the metallization bath. The electrical resistance between the terminal areas of the terminal area arrangement is then repeatedly measured and the time to the formation of a short-circuit contact between the terminal areas is measured.

A device particularly suitable for performing the method according to the is invention comprises a test substrate having at least one terminal area arrangement that comprises two terminal areas disposed at a defined spacing from one another, the terminal areas forming short circuit poles of an electrical measuring circuit comprising a resistance measuring instrument.

To perform the method variant in which, to determine the parameter, the electrical resistance due to the mass of the contact metallization is measured, the test substrate has at least one terminal area, the terminal area forming an electrical conductor of an electrical measure circuit comprising a resistance measuring instrument. A test substrate particularly suitable for performing the method according to the invention or for forming a suitable device has at least one set of terminal area arrangements having a plurality of terminal area arrangements, the terminal area arrangements each having two terminal areas assigned to one another at a defined contact spacing and the contact spacings between terminal areas assigned to one another of various terminal area arrangements being different.

A test substrate structured in this way makes possible both the determination of the concentration of a stabilizing component contained in metallization bath and the determination of the deposition rate of the metallization material on the terminal areas.

If the test substrate comprises, in addition, a plurality of sets of terminal area arrangements, each set of terminal areas being of equal size and the various sets of terminal areas having a different size it is also possible when performing the method to detect effects that are due to the nonlinear behaviour of the diffusion of the stabilizing components into the surface of the terminal areas and that result in an anisotropic deposition on the terminal areas.

A design of the test substrate having a spatial arrangement of the terminal areas that is such that, to form the contact spacing between two terminal areas assigned to one another, the terminal areas are disposed in spaced substrate levels is suitable, in particular, for the case of a strongly anisotropic deposition of the contact material on the terminal areas.

Preferred variants of the method or preferred embodiments of the device suitable for performing the method are described in greater detail below with reference to the drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 4 is a top view of a further embodiment of a test substrate having a plurality of sets of terminal area arrangements comprising terminal areas of different size;

FIG. 5 is a sectional view showing the formation of contact metallizations on terminal areas of a terminal area arrangement of the test substrate shown in FIG. 4 based on one of various different metallization baths;

FIG. 6 is a sectional view showing the formation of contact metallizations on terminal areas of a terminal area arrangement of the test substrate shown in FIG. 4 based on another of various different metallization baths;

FIG. 7 is a sectional view showing the formation of contact metallizations on terminal areas of a terminal area arrangement of the test substrate shown in FIG. 4 based on another of various different metallization baths;

FIG. 8 is a sectional view showing the formation of contact metallizations on FIG. 4 based on another of various different metallization baths;

FIG. 9 is a sectional view showing contact metallizations deposited on terminal areas of different size;

FIG. 10 is a side partially sectional view showing a further embodiment of a test substrate having a spatial arrangement of terminal areas;

FIG. 11 is a plan view of the test substrate shown in FIG. 10;

FIG. 12 is sectional view showing the test substrate shown in FIG. 11 in along the sectional-line path XII—XII.

DESCRIPTION OF THE PREFERRED EMBODIMENTS

Figure 1:
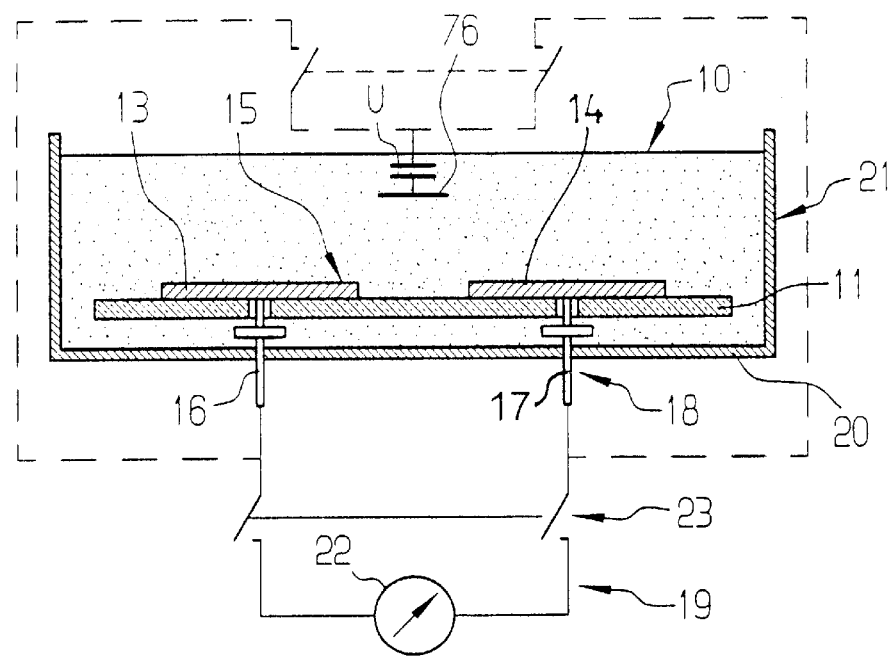
FIG. 1 is a sectional view of a test substrate immersed in a metallization bath prior to the beginning of the deposition of the contact metallizations.

Referring to the drawings in particular, FIG. 1 shows a test substrate 11 inserted in a metallization bath 10 immediately after the insertion into the metallization bath 10 prior to the beginning of the deposition of metallization material 12 dissolved in the metallization bath 10 on a terminal area arrangement 15 of the test substrate 11, said terminal area arrangement being formed by two terminal areas 13 and 14.

The metallization bath shown in FIG. 1 and mentioned below may be a nickel bath that serves, for example, for forming contact metallizations on aluminium terminal areas, which are also described in technical terminology as aluminium pads. The substrate may be formed substantially of silicon, such as is the case, for example, for a chip or wafer.

The terminal areas 13 and 14 of the test substrate 11 are connected in the present case via a contact arrangement 18 by means of two through connections 16 and 17 to an electrical measuring circuit 19. The through connections 16, 17 pass through a container wall 20 of a bath container 21 accommodating the metallization bath 10. The contact arrangement shown here by way of example can also be formed as an immersion contact arrangement without passing through the container wall. The measuring circuit 19 that comprises a resistance measuring instrument 22 is provided with a switch arrangement 23 that makes possible opening and closure of the electrical measuring circuit 19.

Figure 2:
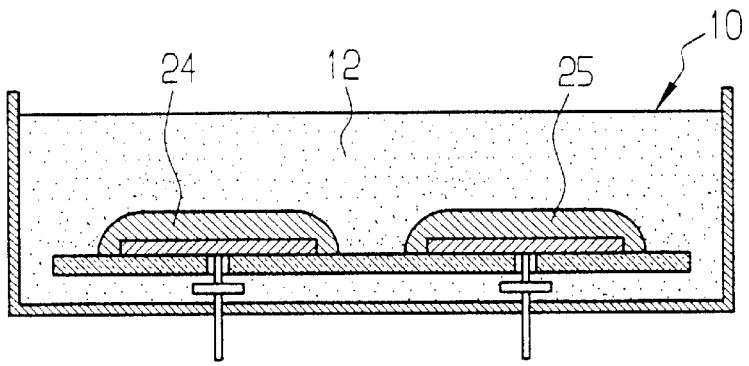
FIG. 2 is a sectional view of the test substrate shown in FIG. 1 in an intermediate stage, with partly formed contact metallizations.

FIG. 2 shows the state of the terminal areas 13, 14 of the test substrate 11 after advanced immersion time, contact metallizations 24, 25 already forming in a clearly visible manner on the terminal areas 13, 14 as a result of wet-chemical deposition of the metallization material 12 from the metallization bath 10.

Figure 3:
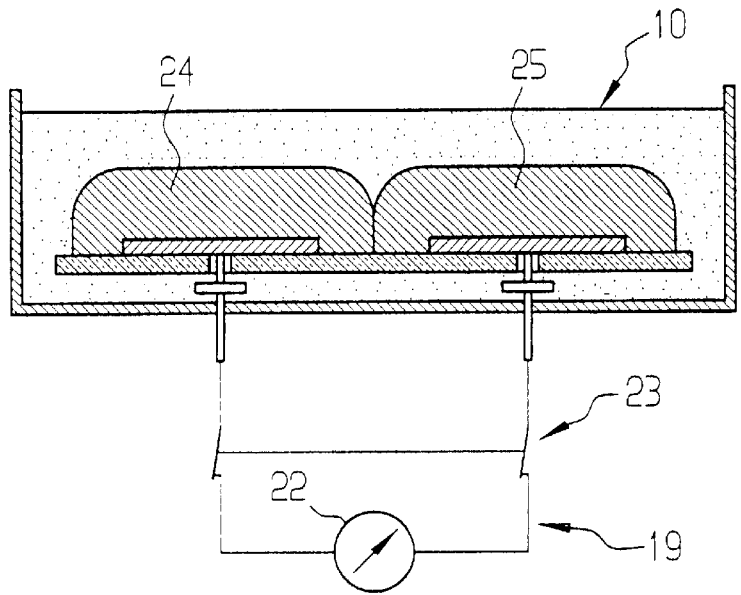
FIG. 3 is a sectional view of the test substrate shown in FIG. 1 in a contact stage of the contact metallizations.

FIG. 3 shows the contact metallizations 24, 25 formed on the terminal areas 13, 14 by deposition of the metallization material 12 at an advanced stage in which the contact metallizations 24, 25 have coalesced with the formation of a contiguous contact and make possible, in this contact state, a short-circuit of the measuring circuit 19 in the closed position of the switch arrangement 23. This instant of coalescence of the contact metallizations 24, 25 can be clearly detected by a drastic drop of the to resistance value measured by the resistance measuring instrument 22.

The abovementioned correlation between the coalescence of the contact metallizations 20 24, 25 and the marked change in an electrical parameter of the measuring circuit 19 makes possible the determination of characteristic parameters for the deposition process that takes place in the metallization bath 10 and that make it possible in a simple manner to monitor the deposition process for the purpose of reproducibly producing contact metallizations of defined size or morphology.

FIG. 4 shows a test substrate 26 comprising three sets 27, 28 and 29 of terminal area arrangements that each have four terminal area arrangements 30 to 33 or 34 to 37 or 38 to 41 having in each case terminal areas 42, 43 and 44 of various sizes, the terminal areas within a set 27 to 29 being equally large. In the test substrate 26 shown by way of example in FIG. 4, contact spacings 45, 46, 47, 48 between the terminal areas 42, 43, 44 assigned to one another by the terminal area arrangements are uniformly graded in such a way that for every set 27, 28, 29 of terminal area arrangements, the contact spacings become larger by an equal extent proceeding from the narrow contact spacing 45 and advancing via the contact spacings 46 and 47 to a contact spacing 48, At the same time, the respective contact spacings 45 to 48 are equally large for the individual sets 27 to 29 of terminal area arrangements.

To explain the different deposition behaviour or its effect on the morphology of contact metallizations 49 to 52, the terminal area arrangements 30 to 33 of the first set 27 of terminal area arrangements are shown in FIGS. 5 to 8 based on a partial sectional view of the substrate 26 in the region of the respective terminal area arrangement 30 to 33. The views in FIGS. 5 to 8 each apply to deposition processes in different metallization baths. FIGS. 5 to 8 each show the morphology of the contact metallizations 49 to 52 in that phase of the method in which an electrically conductive contact is formed between the terminal areas 42 as a consequence of the contact metallizations 49 to 52 that have coalesced over the respective contact spacing 45, 46, 47 or 48 and have resulted from deposition on the terminal areas. At the same time, the metallization baths respectively used have a different concentration of a stabilizing component, with otherwise identical bath composition, said stabilizing component being intended to prevent the decomposition of the metallization bath In the present case, the stabilizer concentration decreases proceeding from the view according to FIG. 5 to the view according to FIG. 8.

To explain fundamentally the effect of the stabilizer concentration of a metallization bath on the morphology of a contact metallization 53 or 54, respectively, reference is made to FIG. 9, in which the effects become still clearer in comparing terminal areas 55, 56 of extremely different size. The finite nature of the terminal areas 55 and 56 results in a differentiated diffusion behaviour in the diffusion of the stabilizer component into the surface of the terminal areas 55 and 56. In the region of the surface the terminal areas 55, 56, at a sufficiently large distance from the peripheries of the terminal areas 55, 56, a substantially linear diffusion behaviour occurs and in the region of the peripheries themselves, a nonlinear diffusion behaviour occurs as a consequence of a peripheral effect. In the region of the peripheries, said nonlinear diffusion behaviour causes an intensification of the inhibition action effected by a stabilizer component, such as, for example, lead, said inhibition action acting against a deposition of the contact material from the metallization bath on the terminal areas 55, 56. A substantially heavier deposition of contact material on the terminal areas 55, 56 is therefore established at a distance from the peripheries of the terminal areas 55, 56 than in the region of the peripheries themselves. This nonuniform deposition is also described as anisotropic deposition. In contrast thereto, in a metallization bath free of stabilizing components, as shown, for example, in FIGS. 1 to 3, a uniform, isotropic deposition of the metallization material occurs on the terminal areas, i.e. in the region of the peripheries the deposition takes place to the same extent as in a region of the terminal areas at a distance from the peripheries.

FIG. 9 now shows a phenomenon that is to be observed, in particular, in metallization baths having high stabilizer concentration and that is also described as "bevelling" in technical terminology. In this case, severe bevels are to be observed in the contact metallizations 53,54 in the region of the peripheries of the terminal areas 55 and 56 or, alternatively, a suppression of the contact metallizations 53, 54 is to be observed at a correspondingly higher stabilizer concentration, said suppression or bevels virtally preventing a growth of the contact material beyond the peripheries of the terminal areas 55, 56. Depending on the size of the terminal area, said "bevelling" also has a decisive effect on the height of a contact metallization 53, 54 that can be achieved by a deposition process. As FIG. 9 in fact clearly shows, proceeding from an identical stabilizer concentration, with a comparatively small terminal area 55, a smaller height of the contact metallization 53 is to be expected compared with a larger terminal area 56 in contrast to the contact metallization 54 deposited on the larger terminal area 56. With a sufficiently high stabilizer concentration, the deposition may even be completely suppressed in the case of a small terminal area.

The above comments made with reference to FIGS. 5 to 9 make it clear that the deposition processes influenced by the stabilizer concentration can be utilized in conjunction with a device shown with regard to its basic principles in FIGS. 1 to 3 also for determining an unknown stabilizer concentration of a metallization bath. For this purpose, the test substrate 26 shown in FIG. 4 can be used, specifically in such a way that the test substrate 26 is introduced for a specified time interval of for example, 10 to 20 minutes into a metallization bath of unknown stabilizer concentration At the same time, the individual terminal area arrangements 27 to 41 are connected to an electrical measuring circuit 19 by means of their respective terminal areas 42,43 or 44 in the way shown in FIGS. 1 to 3, said measuring circuit being periodically closed and opened. Depending on the terminal area arrangements for which electrical contacts result between the contact metallizations grown by deposition on the respective terminal areas within the specified time interval, in a first estimate, qualitative conclusions can be drawn about the stabilizer concentration present in the metallization bath A deposition process does not occur in the case of a terminal area below a certain minimum size and with a sufficiently high stabilizer concentration. If only an electrical contact is detected via the deposited contact metallizations in the case of the terminal area arrangements 30 and 31 at the end of the specified time interval, a comparatively high stabilizer concentration with a correspondingly low deposition rate is present. If on the other hand, an electrical contact is detected in addition in the case of the terminal areas 42 of the terminal area arrangement 32 and 33 assigned to one another at the comparatively large contact spacing 47, 48, a comparatively low stabilizer concentration exists, with a correspondingly high deposition rate. A quantitative determination of the stabilizer concentration going beyond this qualitative evaluation then becomes possible by comparison with reference measurements in which, with a known stabilizer concentration of a metallization bath, a respective correlation has been carried out between the stabilizer concentration and a certain terminal area arrangement having a defined contact spacing.

Since, as was explained, in particular, with reference to FIG. 9, the effect of the stabilizer concentration of a metallization bath on the morphology of a contact metallization is different for terminal areas of different size, the test substrate 26 may be provided, as shown in FIG. 4, with further sets 28 and 29 of terminal area arrangements comprising terminal areas 43 and 44 of different size so that the test substrate 26 makes possible conclusions that are as general as possible about the effects of the stabilizer concentration on the morphology of the contact metallizations, but at least for terminal areas of different size.

FIG. 10 shows a test substrate 57 having terminal area arrangements 58, 59, 60, 61 that each have two terminal areas 62 that are assigned to one another and that, in the case of the individual terminal area arrangements 58 to 61, have a different contact spacing 63, 64, 65, 66 and optionally terminal areas of different size.

As emerges from an overall view of FIGS. 10 and 11, the terminal areas 62, disposed above the carrier plate 67 of the substrate 57, of the terminal area arrangements 58 to 61 are situated at the unsupported end of carrier-arm-type bracket projections 68 to 71 and are situated at the respective contact spacings 63 to 66 opposite the assigned terminal areas 62 in the carrier plate 67. Provided both in the carrier plate 67 and in the bracket projections 68 to 71 are contact conductors 72 that debouch into external contacts 73 that make possible a contacting of the terminal areas 62 through a container wall 74 of a bath container 75, as shown in FIG. 12.

The view according to FIG. 12 makes it clear that, using the test substrate 57, the formation of an electrical contact between two contact metallizations 76 and 77 forming on the terminal areas 62 of the terminal area arrangement 58 is possible not parallel to the surface of the substrate 57, as is the case for the test substrate 26 shown in FIG. 4, but, on the contrary, perpendicular to the surface of the test substrate 57. The abovedescribed method for determining the stabilizer concentration in a metallization bath utilizing the short-circuit forming between the contact metallizations can consequently also be used in those cases where, as shown, for example, in FIG. 9, no growth of the contact metallizations takes place beyond the peripheries of the terminal areas as a consequence to of the deposition process, but only on the surface of the terminal areas. As becomes clear from an overall view of FIGS. 11 and 12, the arrangement in each case of a terminal area 62 of the terminal area arrangements 58 to 61 at the end of the bracket projections 68 to 71 makes possible as insignificant as possible a masking of the carrier plate 67 by the arrangement of the terminal areas 62 disposed above the carrier plate 67 in order to ensure as before good accessibility of the lower terminal area 62 disposed in the carrier plate 67 for the metallization material dissolved in the metallization bath and consequently to impair the deposition process on the lower terminal areas as little as possible.

A possible addition to the device that can be used for performing the method is shown by a dotted line pattern in FIG. 1. In this case, there is provided a counterelectrode 76 for the terminal areas 13 and 14 that makes it possible for a defined potential U to be impressed on the terminal areas 13 and 14. This makes possible an influencing of the electrochemical processes at the terminal areas and, consequently, an adaptation of the device to different metallization media, including, in particular, galvanic metallization media. In the exemplary embodiment shown, the counterelectrode is separated from the terminals only during the measurement process. In addition, the counterelectrode makes it possible to redissolve the metallization deposited on the terminal areas by anodic polarization and thus to prepare the terminal areas for a further measurement cycle. For this purpose, the counterelectrode can be activated after a measurement only for the purpose of regenerating the terminal areas.

What is claimed is:

1. A method for determining a parameter for the reproducible production of raised contact metallizations on terminal areas of a substrate, the method comprising the steps of:

depositing a metallization material in a metallization bath;

introducing a test substrate into the metallization bath, the test substrate having at least two adjacent terminal areas at a defined spacing with respect to each other, with the at least two adjacent terminal areas in direct contact with the metallization bath to deposit metallization material on each of the adjacent terminal areas to build up contact metallizations on each of the adjacent terminal areas; and determining a parameter from a variation in an electrical quantity as a consequence of an electrical contact between the built up contact metallizations resulting from physical contact of the built up contact metallizations on each of the adjacent terminal areas.

2. A method according to claim 1, wherein said parameter is determined from the variation in the electrical resistance of an electrical measuring circuit encompassing the terminal areas.

3. A method for determining a parameter for the reproducible production of raised contact metallizations on terminal areas of a substrate the method comprising the steps of:

depositing a metallization material in a metallization bath;

introducing a test substrate, having at least one terminal area, into the metallization bath with the at least one terminal area in direct contact with the metallization bath to deposit metallization material on the terminal area to build up a contact metallization on the terminal area; and determining a parameter from the measurement of an electrical quantity due to the mass of the contact metallization on the terminal area.

4. A method according to claim 3, in that the parameter is determined from the value of the electrical resistance of an electrical measuring circuit connected to the terminal area.

5. A method according to claim 4, wherein to determine the electrical resistance the measuring circuit is closed only intermittently via a resistance measuring device.

6. A method according to claim 5, wherein the electrical resistance the measuring circuit is closed periodically.

7. A method according to claim 3, wherein a concentration of a bath stabilizer added to the metallization bath is determined as the parameter.

8. A method according to claim 7, wherein to determine the stabilizer concentration, the test substrate is provided with a plurality of terminal area arrangements that each comprise two terminal areas assigned to one another at a defined contact spacing, said terminal areas having one or more of varying contact spacings, different sizes, said test substrate being immersed for a predetermined time interval in the metallization bath during which time interval the electrical resistance between the terminal areas of the respective terminal area arrangements is repeatedly measured and the stabilizer concentration is determined as a function of the maximum contact spacing of the terminal areas with short circuit contact by comparison with contact spacing reference values for known stabilizer concentrations.

9. A method according to claim 3, wherein a deposition rate of the metallization material of the contact metallization in the metallization bath in forming the contact metallizations is determined as the parameter.

10. A method according to claim 9, wherein to determine the deposition rate, the test substrate, which is provided with at least one terminal area arrangement that comprises two terminal areas assigned to one another with a defined contact spacing, is immersed in the metallization bath, the electrical resistance between the terminal areas of the terminal area arrangement is then repeatedly measured and the time to the formation of a short circuit contact between the terminal areas is measured.

11. A device for determining a parameter for the reproducible production of raised contact metallizations on terminal areas of a substrate, the device comprising:

a metallization bath;

a test substrate having at least one terminal area arrangement that comprises two terminal areas disposed at a defined spacing from one another, said test substrate being introduced into the metallization bath with two terminal areas in direct contact with the metallization bath for depositing a metallization material; and an electrical measuring circuit comprising a resistance measuring instrument, said electrical measuring circuit being connected to the two terminal areas.

12. A device according to claim 11, wherein said terminal area forms short circuit poles of said electrical measuring circuit.

13. A device according to claim 11, wherein said terminal area forms a conductor of said electrical measuring circuit.

14. A device according to claim 13, wherein said substrate has at least one set of terminal area arrangements comprising a plurality of terminal area arrangements, the terminal area arrangements each having two terminal areas assigned to one another at a defined contact spacing, the contact spacings being different between terminal areas, assigned to one another, of various terminal area arrangements.

15. The device according to claim 14, wherein a plurality of sets of terminal area arrangements are provided, including terminal area arrangements comprising terminal areas of equal size and the terminal area arrangements comprising terminal areas of different size.

16. The device according to claim 14, wherein a spatial arrangement of the terminal areas is provided in such a way that, to form the contact spacing between two terminal areas assigned to one another, the terminal areas are disposed in spaced substrate levels.

* * * * *